United States Patent [19]

Bender et al.

[11] Patent Number: 5,081,251
[45] Date of Patent: Jan. 14, 1992

[54] STILBENE COMPOUNDS USE IN ANIONIC POLYMERIZATION

[75] Inventors: Dietmar Bender, Schifferstadt; Klaus Bronstert, Carlsberg, both of Fed. Rep. of Germany

[73] Assignee: BASF Aktiengesellschaft, Ludwigshafen, Fed. Rep. of Germany

[21] Appl. No.: 404,206

[22] Filed: Sep. 7, 1989

[30] Foreign Application Priority Data

Sep. 22, 1988 [DE] Fed. Rep. of Germany ....... 3832204

[51] Int. Cl.$^5$ ................. C07C 211/48; C07D 213/10
[52] U.S. Cl. .................... 546/350; 564/305; 564/330; 564/331; 564/433; 564/434; 564/443; 568/631; 568/646; 585/25; 585/435
[58] Field of Search ............... 564/305, 330, 331, 433, 564/434, 443; 568/631, 646; 546/350; 585/25, 435

[56] References Cited

U.S. PATENT DOCUMENTS

| | | | |
|---|---|---|---|
| 3,158,475 | 11/1964 | Cassiers et al. | 564/305 X |
| 3,254,131 | 5/1966 | Landis | 564/305 X |
| 4,335,055 | 6/1982 | Blaser et al. | 564/305 X |
| 4,709,096 | 11/1987 | Sasaki | 564/305 X |
| 4,859,556 | 8/1989 | Saraki | 564/433 X |

FOREIGN PATENT DOCUMENTS 2241304 3/1973 Fed. Rep. of Germany .
2121789 1/1984 United Kingdom .

*Primary Examiner*—Richard L. Raymond
*Attorney, Agent, or Firm*—Oblon, Spivak, McClelland, Maier & Neustadt

[57] ABSTRACT

Stilbene compounds of the general formula Ia, Ib or Ic $$R^1R^2R^3Ar^1\text{—CH}=\text{CH—}Ar^3R^4R^5R^6 \quad \text{(Ia)}$$

$$R^1R^2R^3Ar^1\text{—CH}=\text{CH—}Ar^2R^4R^5R^6\text{—CH}=\text{CH—}Ar^3R^7R^8R^9 \quad \text{(Ib)}$$

$$R^1R^2R^3Ar^1\text{—CH}=\text{CH—}Ar^2(CH_2)_nAr^3\text{—CH}=\text{CH—}Ar^4R^4R^5R^6 \quad \text{(Ic)}$$

where $Ar^1$ to $Ar^4$ are identical or different aromatic or quasi-aromatic radicals and n is from 0 to 20 and where either at least one of the radicals $R^1$ to $R^6$ or $R^9$ is hydrocarbon-solubilizing alkyl, alkoxy, dialkylamino or diarylamino of 4 or more carbon atoms in the alkyl moiety or, if formula Ic contains no radicals $R^1$ to $R^6$, n is not less than 4, are prepared by metalating a toluene/xylene analog $R^1R^2R^3ArCH_3$ or $H_3CR^4R^5R^6ArCH_3$ with an appropriate aldehyde Ar-CHO or dialdehyde OHC-Ar-CHO to form correspondingly substituted metal mono- or dialcoholates which are hydrolyzed/solvolyzed and dehydrated or pyrolyzed, and are used for preparing bifunctional initiators for anionic polymerization.

12 Claims, No Drawings

STILBENE COMPOUNDS USE IN ANIONIC POLYMERIZATION

The present invention relates to novel conjugated aromatic or quasi-aromatic compounds of the general formula I (a, b or c)

$$R^1R^2R^3Ar^1\text{—}CH\text{=}CH\text{—}Ar^2R^4R^5R^6 \qquad (Ia)$$

$$R^1R^2R^3Ar^1\text{—}CH\text{=}CH\text{—}Ar^2R^4R^5R^6\text{—}CH\text{=}CH\text{—}Ar^3R^7R^8R^9 \qquad (Ib)$$

$$R^1R^2R^3Ar^1\text{—}CH\text{=}CH\text{—}Ar^2(CH_2)_nAr^3\text{—}CH\text{=}CH\text{—}Ar^4R^4R^5R^6 \qquad (Ic)$$

where $Ar^1$ to $Ar^4$ are each mono- or bi-dentate aryl or quasi-aryl, to the preparation thereof and to the use thereof in anionic polymerization.

Compounds of this structural type, ie. stilbenes and compounds which may be considered stilbene derivatives, are technically of interest for use as scintillators, fluorescent whitening agents, liquid crystals and initiators for anionic polymerization. For use in the last case, the parent compound is converted by reduction with an alkali metal into a carbanion derivative which reacts with certain olefinically unsaturated monomers (eg. styrene) to give a living polymer.

It is an object of the present invention to provide stilbenes Ia and Ib which have longer alkyl chains or similar groups as direct or indirect substituents ($R^1$ to $R^9$ in the formulae Ia and Ib) and therefore are soluble in hydrocarbons, and compounds of the general formula Ic which may be considered as formed from alkylene bisaryl compounds and for example appropriate toluene derivatives; they have for example the structure $$(R^1R^2R^3Ar^1\text{—}CH\text{=}CH\text{—}Ar^2(CH_2)_n\text{—}Ar^3\text{—}CH\text{=}CH\text{—}Ar^4(R^4R^5R^6)$$

where n is not less than 4 if no other solubilizing radical $R^1$ to $R^6$ is present. Otherwise, n can be zero or an integer of up to 20.

We have found that this object is achieved by novel stilbene compounds of the general formula Ia, Ib or Ic where $Ar^1$ to $Ar^4$ are identical or different aromatic or quasi-aromatic radicals and at least one of the radicals $R^1$ to $R^6$ or $R^1$ to $R^9$ is alkyl, alkoxy, dialkylamino or diarylamino, each of not less than 4 carbon atoms, or/and n is not less than 4.

It is known that compounds of the type of the general formula I are obtainable by Wittig carbonyl olefination (Angew. Makromol. Chem. 29/30 (1973), 307; Chem. Ber. 94 (1961), 907; J. Org. Chem. 24 (1959), 1246) from an aldehyde and a phosphonium ylide and also by reacting Grignard compounds with aldehydes (Recueil des Travaux Chimiques Pays-Bas 72 (1953), 765) and via the pathway of anil synthesis (Hel. Chim. Acta, 52 (1969), 2521; Hel. Chim. Acta, 63 (1980), 1311).

To synthesize the target compounds in industry, the ready availability of the starting materials is a necessary prerequisite which, however, has hitherto largely not been met:

In the case of the Wittig reaction and the reaction of Grignard compounds, it is necessary to use halomethylated starting materials which are difficult to obtain. Alkyl- and alkoxy-substituted chloromethylaromatics are preferably synthesized by chloromethylation which, however, is not feasible in practice for occupational hygiene reasons.

An anil synthesis permits in principle the use or the corresponding methylaromatics which are readily accessible by Friedel-Crafts alkylation. For instance, methyl-substituted carbocyclic aromatics of the biphenyl, terphenyl, stilbene, naphthalene, anthracene, phenanthrene and pyridine series can be converted with appropriate benzalanilines by the anil process to give compounds of the structural type I in a yield of 20-80%. But, starting from simple toluene, the preparation of stilbenes has a yield of not more than 15%. Anil synthesis must therefore be considered a synthetic method which is applicable in particular to conjugated and fused systems and to heterocyclic aromatics.

The compounds according to the invention are advantageously obtained by a method mentioned in passing in J. Org. Chem. 35 (1970), 1288, by starting from easily accessible methyl-containing aromatic compounds which may derive from benzene, pyridine and higher conjugated and fused aromatic systems and in each case a suitable aldehyde. The pathway described hereinafter in detail is suitable with particular advantage for obtaining stilbenes or stilbene analog compounds which have substituted aryl radicals, for example of benzene, naphthalene or pyridine, in particular for example those having longer-chained alkyl radicals or dialkylamino or diarylamino groups as substituents.

The process for preparing compounds of formula types Ia and Ib comprises the following steps:

monometalating or dimetalating toluene, xylene or a similar, aromatic or quasi-aromatic compound having at least one methyl group, reacting the metalated, unsubstituted or $R^1$ to $R^9$-substituted compound $ArCH_2M$ or $Ar(CH_2M)_2$ with an appropriate (similarly unsubstituted or $R^1$- to $R^9$-substituted) aromatic aldehyde $ArCHO$ or dialdehyde $Ar(CHO)_2$ to form the corresponding mono- or dialcoholates IIa, IIb and IIb':

$$R^1R^2R^3ArCH_2CH(OM)ArR^4R^5R^6 \qquad IIa$$

$$R^1R^2R^3ArCH(OM)CH_2ArR^4R^5R^6CH_2CH(OM)ArR^7R^8R^9 \qquad IIb$$

$$R^1R^2R^3ArCH_2CH(OM)ArR^4R^5R^6CH(OM)CH_2ArR^7R^8R^9 \qquad IIb'$$

hydrolyzing or solvolyzing IIa, IIb or IIb' or converting IIa, IIb or IIb' in a conventional manner into an ester compound and dehydrating or pyrolyzing the resulting intermediate.

Compounds Ic can be obtained in a similar manner.

Key compounds are the intermediate which appear, ie. the metalated methylaromatics and the hydroxy or ester hydrolysis/solvolysis product compounds IIa, IIb and IIb'.

Suitable aryls for the purposes of the present invention are for example the radicals of benzene, pyridine, naphthalene, anthracene, phenanthrene, quinoline, isoquinoline, stilbene itself, biphenyl, diphenyl (thio)esters, diphenylalkanes, terphenyl, furan, and pairs of identical or different aryl radicals each separated by a longer alkylene chain.

The basic aromatic structure can here be substituted by one or more solubilizing groups R which under the conditions of the metalation reaction are chemically inert toward the organometallic bases used. Suitable substituents are linear of branched alkyl, alkenyl, aralkyl, aryl or cycloalkyl of for example up to 20 carbon atoms, which may also contain ether bridges, and also N,N-dialkylamino radicals of up to 20 carbon atoms per alkyl group. The alkyl substituents may also be bonded to the aromatic system at two positions and thus form an alicyclic ring. Finally, pairs of aryl radicals can be separated from the other member of a pair by a solubilizing alkylene radical. The substituents are in general not metalated unless a very high excess of metalating agent is used.

In compounds of the general structure Ar—CH$_3$ and CH$_3$—Ar—CH$_3$, Ar is preferably a phenyl, naphthyl or pyridine group monosubstituted or disubstituted by alkyl or N,N-dialkylamino in such a way that the total number of carbon atoms in the substituent is within the range from 4 to 60, preferably from 4 to 30, carbon atoms. The starting materials for the synthesis are advantageously so chosen—if initiators for anionic polymerization are to be prepared—as to produce stilbenes or bis-stilbenes which have longer-chain substituents of the alkane type of corresponding segments, ie. alkylene bridges (not less than about 6–8 carbon atoms long) and which are still soluble in hydrocarbons as mono- or polyanions.

The metalation of the methyl-carrying aromatics can take place at every methyl group present in accordance with

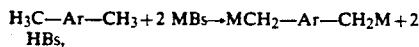

where Bs is the radical of the organometallic base used and M is preferably an alkali metal, in particular lithium or potassium.

Suitable organometallic bases have been described repeatedly (Angew. Chem. 85 (1973), 544; J. Amer. Chem. Soc. 99 (1977), 1473; J. Org. Chem. 51 (1986); 1618; J. Org. Chem. 47 (1982), 3949; J. Org. Chem. 38 (1973), 1491). However, the experiments described therein are concerned with the metalation of methyl-substituted aromatics only, the spectroscopic characterization of the organometallic compounds and the reaction thereof with simple electrophiles, for example dimethyl sulfate. The preparative potential of these nucleophilic compounds for reactions with aromatic aldehydes was not investigated. Nor was an attempt made to clarify to what extent the regioselectivity of the metalation is affected by the presence of other substituents, for example alkyl groups.

Suitable organometallic bases for the hydrogen abstraction process are in particular mixtures of potassium alcoholates and lithium alkyls. Preference is given to mixtures of the potassium salts of linear, branched or cyclic alkyl alcohols of from 1 to 22 carbon atoms and lithium alkyls, for example ethyllithium or n- or sec-butyllithium. It is particularly advantageous to use mixtures of n- or sec-butyllithium and potassium tert-butoxide.

We assume that the metalation proceeds via an organopotassium intermediate.

It is true that the mixing ratio of potassium alcoholate to lithium alkyl can be varied within wide limits, but since only the mixed 1:1 complex acts as a metalating species it is sensible to use stoichiometric amounts of potassium alcoholate and lithium alkyl.

The amount of potassium alcoholate/lithium alkyl base can be varied within the range from 0.1 to 1.5 moles per mole of methyl group, based on the methyl-carrying component. To ensure quantitative conversion of all methyl groups, it is advisable to use the potassium alcoholate/lithium alkyl base in an amount of from 1 to 1.5 moles per mole of methyl.

Suitable solvents for the metalation reaction are straight-chain and branched aliphatic hydrocarbons, for example n-octane or n-hexane, simple of substituted cycloaliphatic hydrocarbons, for example cyclohexane or methylcyclohexane, and any desired mixture of aliphatic and cycloaliphatic hydrocarbons. Aromatic hydrocarbons can logically be used if they have no methyl substituents in the ring. The reaction will proceed at as low as −20° C. with the upper limit being 120° C. and the preferred range being 20°–80° C.

The rate of the metalation is crucially determined by the potassium alcoholate and lithium alkyl component used, the methyl-bearing component and the reaction temperature.

For instance, complete conversion of decyltoluene or hexadecyltoluene in cyclohexane with a mixture of potassium tert-butoxide and n-butyllithium at 40° C. takes 60 minutes. The result is a deep red solution. By contrast, toluenes having short-chain alkyl substituents precipitate after the metalation in aliphatic hydrocarbons and form red suspensions of very viscose, brownish black sediments.

The dimetalation of corresponding dimethylarylene requires a comparatively longer reaction time and/or higher reaction temperature. In the case of hexadecyl-meta-xylene, the double abstraction of hydrogen with a potassium alcoholate/lithium alkyl base is possible by heating at 70° C. for 4 hours. The resulting dipotassium compound, unlike the monopotassium compound of hexadecyl toluene, is insoluble in cyclohexane and forms a dark red/brown suspension.

To metalate the methyl-carrying component with lithium alkyls in the presence or polydentate complexing agents, such as crown ethers or N,N,N',N'-tetramethylethylenediamine, it is advantageous to use a mixture which contains from 0.05 to 1.5 moles of lithium alkyl and from 0.05 to 10 moles of the complexing agent per mole of methylene. Preference is given to using from 1 to 1.2 moles of n- or sec-butyllithium and from 1 to 3 moles of N,N,N',N'-tetramethylethylenediamine per mole of methyl.

The reaction temperature is again within the range from 0° to 100° C., preferably within the range from 20° to 70° C.

The rate of hydrogen abstraction is likewise determined by the methyl-carrying component and the reaction temperature; in general, a reaction time of 1–8 hours is required.

To prepare compounds of the formula I (a, b or c), the organometallic compound obtained is reacted with an aromatic aldehyde:

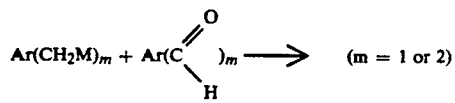

The result obtained is an alcoholate of the formula IIa or IIb or IIc

    IIA

ArCH(OM)CH₂ArCH₂CH(OM)Ar   IIb

ArCH₂CH(OM)ArCH(OM)CH₂Ar   IIb' whose alcoholate function is converted, ideally in situ, by reaction with acetic anhydride, water, acetyl chloride, carbon disulfide/methyl iodide or chlorocarbonic esters into hydroxyl or a thermally or catalytically eliminable group of the general formula —OE. Preference is given to water and acetic anhydride; in the latter case a 1–2-fold excess is used:

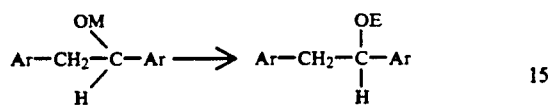

where E is hydrogen or an eliminable group, for example an acyl (in particular acetyl) or (thio)carbonic acid radical. The organometallic compound is advantageously reacted with the aldehyde in stoichiometric amounts. However, it is also possible to use one of the reactants in excess. The aldehyde is added undiluted or as a concentrated solution in a solvent, for example diethyl ether or benzene. The reaction will proceed at as low a temperature as from −30° to −40° C. After the aldehyde has been added, the suspension/solution of the organometallic compound loses its deep color.

After the workup, the intermediate is converted catalytically or thermally (Houben-Weyl volume 5/1b) into the target compound of the general formula I (Ia or Ib) according to the invention.

Preferred leaving groups are water and acetic acid, water being preferably eliminated catalytically by means of acids, acetic acid by contrast preferably thermally at 300° C. The progress of the elimination reaction can be monitored by noting the acetic acid or water separated off. In the catalytic elimination reaction, it is advantageous to use an entrainer and to collect the water formed in a water separator. Suitable catalysts for the water elimination reaction are phosphoric acid and triphenyl phosphite; the reaction takes for example 1–8 hours at 180° C. Both thermal and catalytic elimination lead in the case of stilbenes where each Ar is phenyl to the trans product in a selectivity of about 90%. To purify the target compound, it is possible to resort to gel or adsorption chromatography, distillation and/or crystallization.

The alkyl toluenes used below in the Examples were prepared by Friedel-Crafts alkylation from toluene and 1-alkenes. The alkylation gave isomer mixtures which, according to ¹-NMR and ¹³C-NMR spectroscopy, consist of ortho-, meta- and para-alkyl toluenes having skeletally isomeric alkyl groups. The main products are para- and meta-alkyl toluenes containing alkyl chains which are branched in the 1- or 3-position. These isomer mixtures were used in the metalation reactions without further separation.

The solvents (cyclohexane, hexane, tetrahydrofuran) were distilled over n-butyllithium and a small amount of styrene—as an indicator—to free then from impurities.

Nitrogen was washed with a mixture of white mineral oil, 1% by weight of styrene and 5% by weight of lithium butyl.

The aldehydes used were used without additional purification in the available purity of about 98%.

The metalating agent used was commercial n-butyllithium as a 1.6N solution in hexane.

Potassium tert-butoxide was used in a commercial form in a purity of 95%.

Analytical

The purity of the substance was checked by means of HPLC (HPLC system from Merck-Hitachi, UV detector 655 A-22, Erma RI detector ERC 7510, 4 mm column Lichrogel PS-4, THF as mobile phase).

The molecular weight of the catalysts was checked by correlation against HPLC calibrations involving mono-, di-, oligo- and polystyrene.

EXAMPLE 1

Preparation of a stilbene of the formula

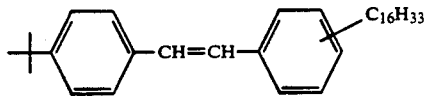

In a six-liter glass reactor, equipped with a cooling-/heating jacket, a floor outlet, a Teflon stirrer and a condenser, 95.4 g (0.85 mol) of potassium tert-butoxide are admixed under nitrogen with 850 ml of cyclohexane and 530 ml (0.85 mol) of n-butyllithium dissolved in hexane. 269.2 g (0.85 mol) of hexadecyl toluene are added dropwise at 20° C. The blackish brown suspension is stirred at 20° C. for 16 hours and then admixed at 10° C. with a solution of 140 g (0.85 mol) of 4-tert-butyl-benzaldehyde in 100 ml of cyclohexane added dropwise. During the addition (over 45 minutes) the color changes from blackish brown to yellow.

The mixture is subsequently stirred for 30 minutes and then poured into 1.2 l of 1N hydrochloric acid. The organic phase is separated off, washed with water until neutral, dried and freed from low boilers under reduced pressure. Thereafter the distillation residue is introduced into a 1-liter flask equipped with a water separator and a dropping funnel.

10 ml of triphenyl phosphite are added as water elimination catalyst, followed by 100 ml of n-octane as entrainer. The mixture is heated to 180° C., and the reaction is monitored by noting the amount of water separated off. The residue is then washed with water until neutral, dried and subjected to fractional distillation. 319 g (81.6%) are obtained in a purity of 99.7% at a crossover temperature of 245°–280° C. under a pressure of 0.08 mbar.

EXAMPLE 2

Preparation of a stilbene of the formula

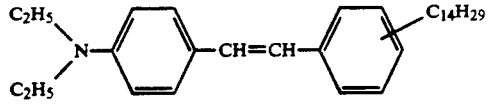

A six-liter glass reactor equipped with a cooling-/heating jacket, a floor outlet and a Teflon stirrer is charged under nitrogen with 137 g (1.22 mol) of potassium tert-butoxide, 1 l of cyclohexane and 320 g (1.11 mol) of tetradecyl toluene, followed in the course of 25 minutes by 760 ml of a 1.6N solution of (1.22 mol) of n-butyllithium in hexane. In the course of the addition, the reaction mixture heats up to 40° C. It is subsequently stirred at that temperature for 60 minutes, cooled down to 10° C. and admixed with a solution of 216 g (1.22 mol) of 4-diethylaminobenzaldehyde in 800 ml of cyclohexane added dropwise at such a rate that the internal temperature constantly remains within the range 10°-15° C. During the addition, the color changes from blackish brown to bright yellow. The mixture is subsequently stirred for 30 minutes and then admixed with 260 g (2.4 mol) of acetic anhydride added dropwise, followed by 2 l of water. The organic phase is separated off and washed with water until neutral. After the solvent has been distilled off, the mixture is heated at 300° C. for about 2 hours and acetic acid is distilled off until separation ceases. The residue is then subjected to fractional distillation. 447 g (90%) of the target compound are obtained in a purity of 99.5% at a boiling temperature of from 270° to 298° C. under a pressure of 0.5 mbar.

EXAMPLE 3

Example 1 is repeated to react 247 g (0.78 mol) of hexadecyltoluene with 0.86 mol of potassium tert-butoxide and 0.86 mol of n-butyllithium in 1000 ml of cyclohexane. 134 g (0.86 mol) of 1-naphthaldehyde are added dropwise at 10° C. to the blackish brown solution. The reaction mixture is subsequently stirred for 60 minutes and admixed with 184 g (1.8 mol) of acetic anhydride, worked up with water and freed by distillation from organic low boilers. To eliminate acetic acid, the mixture is heated at 300° C. for 3 hours under a pressure of 100 mbar. The residue is then subjected to fractional distillation in an oil pump vacuum. 298 g (84%) are obtained of the target compound at 242°-266° C./0.07 mbar in a purity of 97%. Subsequent chromatography over 0.063-0.2 mm silica gel using a mixture of 5% of toluene and 95% of cyclohexane as mobile phase leaves 251 g (73%) of the target compound in a purity of 98.6%:

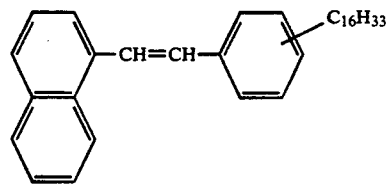

The compounds listed in the Table below were prepared in a similar manner from the particular starting materials shown. Other compounds of this type are easily obtainable by similar methods.

TABLE 1

| Example No. | Methyl compound | Aldehyde | Equivalents of n-BuLi/t-BuOK | Product |
|---|---|---|---|---|
| 1 | $C_{16}H_{33}$—⌬—$CH_3$ | OHC—⌬—⊢ | 1.1 | $C_{16}H_{33}$—⌬—CH=CH—⌬—⊢ |
| 2 | $C_{14}H_{29}$—⌬—$CH_3$ | OHC—⌬—N($C_3H_5$)($C_2H_5$) | 1.1 | $C_{14}H_{29}$—⌬—CH=CH—⌬—N($C_2H_5$)($C_2H_5$) |
| 3 | $C_{16}H_{33}$—⌬—$CH_3$ | OCH-naphthyl | 1.1 | $C_{16}H_{33}$—⌬—CH=CH-naphthyl |
| 4 | $C_{10}H_{21}$—⌬—$CH_3$ | OHC—⌬ | 1.1 | $C_{10}H_{21}$—⌬—CH=CH—⌬ |
| 5 | $C_{14}H_{29}$—⌬—$CH_3$ | OHC—⌬—O—$CH_3$ | 1.1 | $C_{14}H_{29}$—⌬—CH=CH—⌬—$OCH_3$ |
| 6 | $C_{16}H_{33}$—⌬—$CH_3$ | OHC—⌬ | 1.1 | $C_{16}H_{33}$—⌬—CH=CH—⌬ |
| 7 | $C_8H_{17}$—⌬—$CH_3$ | OHC—⌬—$(CH_3)_3$ | 1.1 | $C_8H_{17}$—⌬—CH=CH—⌬—$C(CH_3)_3$ |

TABLE 1-continued

| Example No. | Methyl compound | Aldehyde | Equivalents of n-BuLi/t-BuOK | Product |
|---|---|---|---|---|
| 8 | $C_{14}H_{29}$-C$_6$H$_4$-CH$_3$ | 2-OCH$_3$-C$_6$H$_4$-CHO | 1.0 | $C_{14}H_{29}$-C$_6$H$_4$-CH=CH-C$_6$H$_4$-OCH$_3$ |
| 9 | $C_{10}H_{21}$-C$_6$H$_4$-CH$_3$ | 2-OCH$_3$-C$_6$H$_4$-CHO | 1.0 | $C_{10}H_{21}$-C$_6$H$_4$-CH=CH-C$_6$H$_3$(OCH$_3$)-OCH$_3$ |
| 10 | 2-methylnaphthalene | 4-(C(CH$_3$)$_3$)-C$_6$H$_4$-CHO | 1.0 | 2-naphthyl-CH=CH-C$_6$H$_4$-C(CH$_3$)$_3$ |
| 11 | (CH$_3$)$_3$C-C$_6$H$_4$-CH$_3$ | 1,1,4,4-tetramethyl-6-methoxy-tetralin-CHO | 1.0 | (CH$_3$)$_3$C-C$_6$H$_4$-CH=CH-(tetramethyl-tetralinyl) |
| 12 | 4-picoline | 4-(C(CH$_3$)$_3$)-C$_6$H$_4$-CHO | 1.0 | 4-pyridyl-CH=CH-C$_6$H$_4$-C(CH$_3$)$_3$ |

TABLE 2

| Example No. | Crude yield after distillation | Pure yield after chromatography (purity) | bp./pressure | Eliminated group* |
|---|---|---|---|---|
| 1 | 81% (99.7%) | — | 245–280° C./0.08 mbar | W |
| 2 | 90% (99.5%) | 77% (100%) | 270–298° C./0.5 mbar | A |
| 3 | 84% (97%) | 73% (98.6%) | 242–266° C./0.1 mbar | A |
| 4 | 95% (—) | 83% (99%) | 218–222° C./0.1 mbar | A |
| 5 | 79% (98.2%) | 68% (99.5%) | 261–270° C./0.2 mbar | A |
| 6 | 77% (96.4%) | 34% (99.6%) | 227–248° C./0.05 mbar | A |
| 7 | 73% (—) | 63% (99.0%) | 217° C./0.05 mbar | W |
| 8 | 64% (—) | 53% (99.4%) | 238° C./0.2 mbar | A |
| 9 | 63% (98.9%) | — | 231–236° C./0.1 mbar | A |
| 10 | 75% (99.0%) | 65% (99.0%) | mp. 130° C. | A |
| 11 | 80% (99%) | — | | A |
| 12 | 60% (95%) | — | 180–202° C./1 mbar | A |

*W = Water
A = Acetic acid

EXAMPLE 13

Preparation of

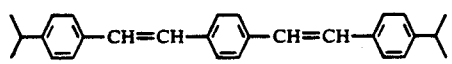

In a 1-l three-necked flask equipped with a reflux condenser and dropping funnel, 44.8 g (0.4 mol) of potassium tert-butoxide, 200 ml of cyclohexane and 53.6 g (0.4 mol) of 4-isopropyltoluene are admixed under nitrogen with 250 ml of a 1.6N solution of (0.4 mol) of n-butyllithium in hexane. The mixture is subsequently stirred at 60° C. for 2 hours, cooled down to 10° C. and admixed at that temperature with a solution of 20.14 g (0.15 mol) of tetraphthaldialdehyde in THF added dropwise. The reaction solution is subsequently stirred at room temperature for 30 minutes and then admixed with 1 mol of acetic anhydride added dropwise. After an aqueous workup, the solvents are distilled off under reduced pressure, and the residue is heated at 300° C. for 60 minutes. Distillation in an oil pump vacuum gives 30 g (54%) of a yellow solid which is 80% target compound. Two crystallizations from ethanol leave 15 g (27%) of the desired product in a purity of 98.9%.

There now follow remarks concerning the use of stilbenes preparable according to the invention:

It is known to use organoalkali metal compounds as catalysts for the anionic polymerization of preferably alkenylaromatics and/or dienes. It is particularly advantageous to use lithium alkyls, since they are comparatively stable and, unlike the corresponding sodium or potassium alkyls, are also soluble in hydrocarbons and permit polymerizations therein. Living polymers having lithium groups are convertible with suitable reagents into terminally functionalized polymers, for example into those having —OH, —SH or amino groups, in high yields. These reactions are best performed in a reaction medium consisting mainly of hydrocarbons.

While known monofunctional lithium alkyls meet all requirements as catalysts for anionic polymerization, known bifunctional initiators have defects. These catalysts, in particular ether-free or low-ether ones, are required in the preparation from dienes of polymers which are functionalized at both chain ends and which preferably contain the dienes in 1,4-configuration.

Polyfunctional initiators of lithium are prepared for example by treating polyfunctional halogen compounds with metallic lithium in ethers. If, however, an attempt is made to remove the ether, a large part of the activity is lost and the catalysts become insoluble. Another form of preparation is the addition of lithium to fused or other aromatic ring systems, for example naphthalene, biphenyl, etc., or to polyaryl-substituted ethylenes such as 1,1-diphenylethylene or stilbene. These reactions are described for example in U.S. Pat. No. 3,170,903.

This reaction is likewise only realizable in ethers or other polar solvents. The presence of these solvents, however, leads in the polymerization of dienes to polymers where the dienes predominantly end up in the 1,2- or 3,4-configuration, which is why such polymers have less desirable properties, including high glass transition temperatures, oxidation sensitivity, crosslinking vulnerability and low thermal stability in processing.

To avoid these properties it has been proposed that after the preparation the ethers be removed by distillation or by precipitating the initiators with hydrocarbons. However, this has the disadvantage that the initiators partly decompose. Moreover, they are insoluble in hydrocarbons, so that a disproportionately large amount of initiator is required for the polymerization and polymers having a broad molecular weight distribution are formed.

To overcome these disadvantages, U.S. Pat. No. 3,377,404 (P. Zelinsky) proposes that the dilithium initiators initially formed by reaction of polyhalogen compounds, polyfused aromatics or polyarylated ethylenes with ethers be solubilized in a 2nd reaction steps by the addition of diolefins and that only thereafter the ether be distilled off.

It is true that the catalysts formed are soluble in hydrocarbons, but the diolefins required for this purpose are virtually exclusively incorporated in the 1,2- or 3,4-configuration. Furthermore, the catalyst is to some extent decomposed in the course of this operation, so that the polymer prepared are only partly polyfunctional.

Other known bifunctional initiators are produced by addition of lithium alkylene on starting compounds which contain 2 double bonds. As a consequence of incomplete reaction or inaccurate metering they frequently contain an amount of the undesirable monofunctional catalyst. Nor are they always sufficiently active, so that they react incompletely in the initiation reaction and/or give rise to polymers having an undesirably broad molecular weight distribution.

It is a specific object of the present invention to provide highly active, stable bifunctional alkali metal initiators which do not contain any monofunctional portions and which are soluble even in media consisting wholly or predominantly of hydrocarbons, to devise a process suitable for the preparation thereof, and to use these catalysts for preparing diterminally grown polymers which may or may not be functionalized.

We have found that this object is achieved according to the invention when the stilbenes obtainable by the above-described process, in particular the substituted stilbenes, are reduced with an alkali metal, in particular lithium, and the resulting bisalkali metal compound is used as a catalyst.

The simplest stilbenes suitable for the purposes of anionic polymerization have the general structure

$$R^1,R^2,R^3Ar^1—CH=CH—Ar^2R^4,R^5,R^6 \quad \text{(Ia)}$$

where $Ar^1$ and $Ar^2$ are identical or different aromatic, even polycyclic, ring systems with or without nitrogen. $Ar^1$ and $Ar^2$ can each be for example phenyl, naphthyl, diphenyl, phenantryl, anthranyl, diphenyl ether, pyridyl, quinolyl and the like. Preferably, $Ar^1$ and $Ar^2$ are each phenyl or naphthyl.

$R^1$ to $R^6$ (ie. R in general) are each hydrogen or linear or branched alkyl, alkenyl, aralkyl or cycloalkyl of from 1 to 25 carbon atoms, which may also contain chemically inert substituents such as ether linkages or tertiary amino. Furthermore, the substituents may alternatively form ring type linkages to $Ar^1$ to $Ar^2$, which, however, must have 3 or more aliphatic carbon atoms. However, the substituents $R^1$ to $R^6$ must together contain from 4 to 60, preferably from 9 to 30, carbon atoms.

If fewer than 4 carbon atoms are in the substituents, the solubility of the catalysts in hydrocarbons is not sufficiently increased. If diene polymers or copolymers are to be prepared in solvents which contain no or only a very small amount of ether (from 0 to 3 moles of ether per mole of polymerization-active lithium), initiators having substituents of more than 8 carbon atoms should be used.

Of the substituents $R^1$–$R^6$, those which have a predominantly linear structure with little branching have a better solubilizing effect than highly branched substituents. For instance, a catalyst formed from stilbene which carries a decyl radical on a benzene nucleus is more soluble in hydrocarbons than a catalyst formed from a stilbene where $R^1$ is t-butyl and $R^4$ and $R^5$ form a fused-on hydrogenated tetramethylcyclohexyl ring (cf. Table 3 below). The most suitable structure must be determined for each case.

Compounds Ib and Ic, which are described at the beginning, are subject mutatis mutandis to the foregoing remarks.

Suitable compounds for the purposes of the present invention are for example ring-alkylated derivatives of cis- or trans-stilbene, or mixtures thereof,

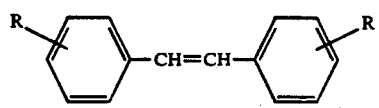

of 1-phenyl-2-naphth-(1-8)-yl ethylene, of 1-phenyl-2-pyrid-(2-5)-yl ethylene and of other derivatives of ethylene such as

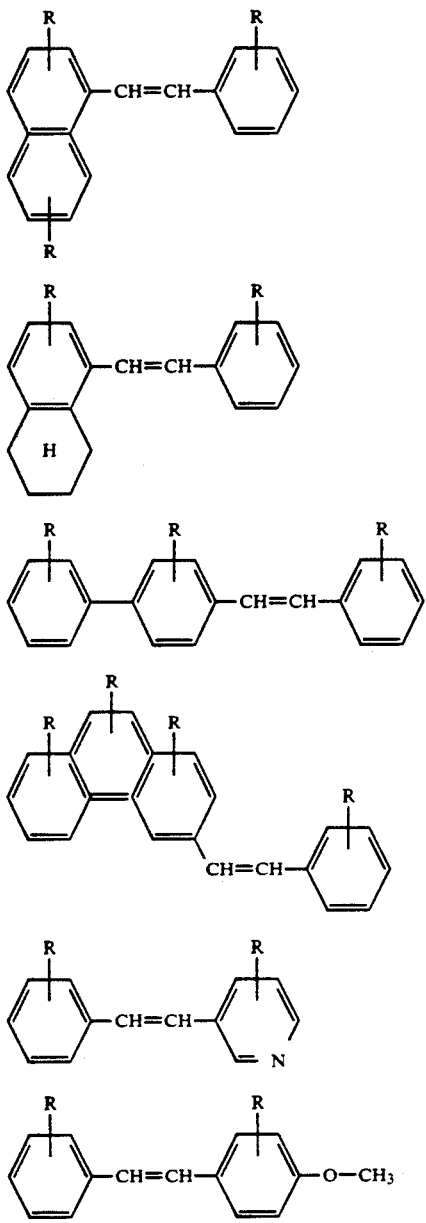

An impressive example of such a compound (which is easily preparable and usable with advantage) is

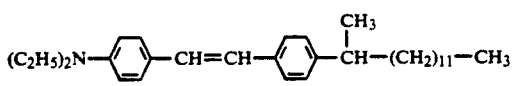

This list is merely illustrative and not complete. Particular preference is give to phenyl and naphthyl as $Ar^1$ and $Ar^2$, to linear or branched alkyl radicals, cycloalkyl radicals, dialkylamino radicals and/or ether groups of together from 8 to 30 carbon atoms as $R^1$ to $R^6$ and hydrogen as $R^1-R^5$; that is, for example to derivatives of cis- or trans-stilbene or of 1-phenyl-2-(1-naphthyl) ethylene, which carry on the aromatic rings from one to 3 aliphatic substituents which together contain more than 8 but fewer than 30 carbon atoms and may or may not contain tertiary nitrogen.

The exothermic metalation of the 1,2-diarylethylenes according to the invention is effected by reacting them in the presence of an ether, of a tertiary amine and if necessary of an aliphatic, alicyclic and/or aromatic solvent with an alkali metal at from −20° to +70° C., preferably at from 0° to 40° C. An advantage of the 1,2-diarylethylenes to be used according to the invention, which have more than 4 carbon atoms in the substituents, lies in the fact that full conversion is obtained in the reaction even with comparatively small amounts of polar solvent in the presence of relatively large amounts of hydrocarbons. However, the amount of ether or tertiary amine present in the reaction mixture should be greater than 3 moles per mole of substituted 1,2-diarylethylene in order to ensure an adequate rate of reaction and full conversion. In addition, inert hydrocarbons may be present in the reaction medium in similar or larger amounts. It is possible to use such initiators directly without removal of the polar solvent for many purposes, for example if the diene polymer is subsequently to be hydrogenated and the hydrogenation product is not to be crystallized.

Particularly highly suitable aliphatic ethers are for example dimethyl ether, diethyl ether, dipropyl ether, dibutyl ether, diisopropyl ether, t-butyl methyl ether and the like, and also alicyclic ethers such as tetrahydrofuran and the like. The reaction is swift even at room temperature and will frequently have ended within 15-60 minutes, during which more than 80% by weight, preferably more than 95% by weight, of the starting compound will have been converted. If less suitable aromatic ethers are used, such as anisole or phenetole, the reaction takes more than 10 times as long. As a consequence of undesirable side reactions, the metal content of the reaction medium is then frequently much higher than the level of polymerization activity.

Suitable tertiary amines are for example trialkylamines, such as triethylamine, trimethylamine or dimethylamine, but also alicyclic or aliphatic-/aromatic amines such as N-methylpiperidine or dimethylaniline.

The reaction is advantageously carried out with thorough mechanical mixing, for example because lithium, as a consequence of its low density, floats on top of the surface of the liquid reaction medium.

After the metalation reaction, volatile ethers or amines may be distilled off under reduced pressure, although 70° C., preferably 25° C., should not be exceeded. Advantageously, hydrocarbons which have a higher boiling point than the ethers or amines are also present. It is then possible to reduce low-boiling aliphatic ethers, for example dimethyl ether, diethyl ether, diisopropyl ether, THF or t-butyl methyl ether, or low molecular weight tertiary amines, for example triethylamine, to residual levels of less than 0.1 mole of ether per mole of polymerization-active lithium without difficulties. The solubility of the catalysts according to the invention is usually preserved if the substituents $R^1-R^9$ have more than 8 carbon atoms and as long as not less than 2 moles of ether are present per mole of polymerization-active lithium/alkali metal. If all of the ether is distilled off, such catalysts, which are prepared from alkyl stilbenes having substituents of from 4 to 8 carbon atoms, become sparingly soluble and precipitate as a whole or in part.

If such suspensions are used for polymerizations, the solids will dissolve in time. However, relatively broad molecular weight distributions will form. Catalysts formed from stilbenes having long, predominantly linear or only lightly branched alkyl groups and more than 8 carbon atoms in the substituents $R^1-R^9$ remain in solution. The most suitable configuration also depends on the radical Ar, and must be determined from case to case.

Solutions of catalysts which contain little or no alicyclic or aliphatic ethers or those which contain only aromatic ethers, such as anisole or phenetole, or tertiary amines form polymers where the dienes are predominantly in the 1,4-configuration. The polymers formed usually have a broader molecular weight distribution and higher molecular weights (determined by GPC) than from the use of monofunctional initiators, where the experimental molecular weights conform relatively closely to those expected arithmetically from the monomer/catalyst ratio.

All solvents and the substituted 1,2-diarylethylenes according to the invention must be freed from impurities prior to use. A suitable method is for example distillation over a metal alkyl such as aluminum triethyl under an inert gas, for example dry, oxygen-free nitrogen or argon.

The reaction to form the catalysts has hardly any competition from lithium-consuming side reactions. Every mole of 1,2-diarylethylene used results in approximately 1 mole or polymerization-active centers; this polymerization activity, which will hereinafter be referred to as PA, can be determined by titrating the solution under inert conditions with i-propyl alcohol until there is a change of color to colorless, and it is in general in good agreement with the alkali metal content of the solution.

The reaction of the 1,2-diarylethylenes with an alkali metal gives 1,2-di(alkali metal)-1,2-diarylethane derivatives which have an intensive color in solution. The color varies with the starting material and is between dark brown and bluish black.

The catalysts according to the invention are highly suitable for the polymerization of vinylaromatics, such as styrene and its derivatives with alkyl substitution in the ring and/or in the α-position, and of dienes such as butadiene, iosprene, 2,3-dimethylbutadiene, piperylene and others. The polymerization can be carried out in any solvent which is also used for monofunctional initiators. Aromatics such as benzene or toluene are highly suitable solvents. However, they have specific disadvantages such as carcinogeneity (benzene) or a chain-transferring effect (toluene) which are not possessed by aliphatic solvents such as cyclohexane or hexane and the like.

The start of the polymerization with catalysts according to the invention is somewhat more difficult than with monofunctional catalysts. It is facilitated by polymerizing diolefins and vinylaromatics with readily hydrocarbon-soluble species of the catalysts according to the invention in the presence of small amounts, for example 1-6 moles per mole of PA, of ethers or tertiary amines. Polymers are then formed which have a narrow molecular weight distribution and approximately the molecular weight to be expected arithmetically from the monomer/initiator ratio in an anionic polymerization with monofunctional initiators. In the presence of ethers or amines, however, the polymers end up with an increased proportion of dienes in the 1,2-configuration. If the presence of polar solvents is dispensed with in order to obtain a high proportion of diolefin in the 1,4-configuration, initiation with the initiators according to the invention is slower. The results are bifunctionally growing polymers having a relatively broad molecular weight distribution and a molecular weight which is higher than that predicted arithmetically. In some instances, even, 2 polymer peaks are measured side by side. The molecular weight distribution can be made narrower again by polymerizing in the presence of 0.1-1 mole of an aliphatic lithium alcoholate per mole of PA (U.S. Pat. No. 4,754,329, EP-A-210,016). This addition does not affect the configuration of the incorporated diolefins.

Using bifunctional catalysts it is possible to prepare block copolymers in fewer stages than with monofunctional initiators. If for example butadiene and styrene are polymerized in succession, these 2 stages give 3-block copolymers which is properties correspond to those polymers of the same composition which have been prepared in a conventional manner with a monofunctional catalyst in a 3-stage polymerization sequence of

Styrene→Butadiene→Styrene.

Following oxidative degradation of the polybutadiene moiety of the polymer with osmium tetroxide (cf. Angew. Makromol. Chem. 26 (1972), 207), the remaining polystyrene blocks are found to have the same molecular weight in both cases.

The corresponding sodium and potassium catalysts are less readily soluble in hydrocarbons. Nonetheless, they can be used for example to polymerize styrene in cyclohexane or other hydrocarbons. However, the resulting molecular weight distributions are broader than with lithium catalysts.

The viscosity of living polymer solutions prepared with initiators according to the invention is for the same molecular weight much higher than that of living polymers prepared with monofunctional catalysts, since the polar, ionic chain ends form a reversible, physical network as a consequence of association. The lower the ether content of the solvent mixture, the stronger the association. It is enhanced by conversion of the carbanion end groups with terminating reagents into for example lithium carboxylate, lithium amide, lithium alcoholate or lithium thiolate end groups to such an extent that gelation occurs even at low polymer concentrations and molecular weights to form an aspic-like mass. By expending a great deal of stirrer energy and applying high torque it is possible to mix the mass through to obtain complete conversion. If this gel has water, alcohol or other compounds with active hydrogens added to it, the ionic network is destroyed and the viscosity of the solution decreases by several orders of magnitude.

The functionalization of the diterminally grown living polymers prepared with the catalyst according to the invention is possible in high yields in the presence or absence of small amounts of polar solvent. Reactions to functionalize the living chain ends are known. Suitable functionalizing reagents are for example oxiranes, which provide terminal primary or secondary hydroxyl functions (cf. U.S. Pat. No. 3,786,116), or thiiranes, whereby terminal thiol groups can be introduced. According to EP-A-0,211,395 or European Patent Application 87 103 893.1, it is possible to obtain polymers which have at least one amino group at the end of the chain. The reactions are described in detail in the cited references, so that no description is necessary here, although it may in some instances be evident from the Examples below.

The polymers according to the invention, if formed wholly or partly from dienes, can be hydrogenated to make all or some of the aliphatic double bonds disappear. The hydrogenation is carried out with the aid of molecular hydrogen and catalysts based on metals or metal salts of subgroup 8 of the periodic table, either in a homogeneous phase or in a heterogeneous phase. The techniques are known and are described for example in U.S. Pat. No. 3,113,986, DE-B-1,222,266, DE-A-2,013,263, DE-B-1,106,961 and DE-A-1,595,345.

Polymers with mercapto, hydroxyl or amino functionalization at both ends of the chain are of particular interest for use as prepolymers for polyurethanes, epoxy resins and other resins or for the modification thereof. The preparation of epoxy resins and of elastomeric polyurethanes composed of a hard segment of aromatic polyisocyanates and a soft segment of functionalized flexible macromolecules is known and described by H. P. Elias in Makromoleküle, 4th edition (1981), pages 778-780 and 809-812, Hüttig and Wepf Verlag, Basle-Heidelberg-New York and the references cited therein.

Terminally amino- or hydroxyl-functionalized polymers prepared according to the invention from dienes and/or vinylaromatics can be crosslinked for example with diisocyanates and other reagents. Solutions of such polybutadienes to which diisocyanates have been added and which are then cast onto siliconized paper and dried produce in the case of polymers composed predominantly of dienes elastic, dry, hydrocarbon-insoluble films which can be peeled off the backing and which have high reversible stretch properties.

Polybutadienediols used as soft segments in thermoplastic polyurethanes are notable for particularly good separation of hard and soft segments, which is desirable for application and processing reasons, as is confirmed by Becker and Braun, Kunststoffhandbuch volume 7, Polyurethane, page 33 (1983), 2nd edition Hanser Verlag, Munich-Vienna. For the same weight average molecular weight, such oils prepared according to the invention have on account of their narrow molecular weight distribution a lower viscosity than known prepolymers, such as free-radical polymerized telechelic polybutadiene oils, polytetrahydrofuran or polyesters. They therefore have better processing properties.

Polymers obtained according to the invention have in general weight average molecular weights Mw of from 500 to 500,000, preferably from 3000 to 130,000, determined by gel permeation chromatography (GPC) and compared with standardized calibration polymers (cf. G. Glökner, Polymercharakterisierung durch Flüssigkeitschromatographie, Verlag A. Hüthig, Heidelberg, (1982)). The measurement takes place in a 0.25% strength by weight tetrahydrofuran solution at 23° C. with a flow rate of 1.2 ml/min. The molecular weight is advantageously determined prior to functionalization, since some functionalized polymers are adsorbed by GPC columns, thereby rendering these columns unusable.

The polymers are worked up in a conventional manner, for example by precipitating with a nonsolvent, by evaporating the solvent or by steam distillation. Devolatilization on a devolatilization extruder is also possible.

The stilbene derivatives used hereinafter were prepared in the manner described above, but for experimental purposes can also be prepared by other known methods of organic chemistry.

The Examples make use of the following substituted 1,2-diarylethylenes as starting materials, predominantly in the trans configuration.

TABLE 3

| Example | Structure of 1,2-diarylethylene | MP | BP | Purity by HPLC | Preparation |
|---|---|---|---|---|---|
| A | (phenyl)–CH=CH–(p-t-butylphenyl) | 89-99° C. | — | 97.47% | Benzylmagnesium chloride + p-t-butylbenzaldehyde → dehydration → recrystallization |
| B | (p-t-butylphenyl)–CH=CH–(p-t-butylphenyl) | 173-176° C. | 187-213° C. 0.08 mbar | 97.45% | t-Butylbenzylmagnesium chloride + p-t-butylbenzaldehyde → dehydration → recrystallization |
| C | (p-t-butylphenyl)–CH=CH–(p-isopropylphenyl) | 118-121° C. | 174-184° C. 0.04 mbar | 99.48% | p-t-Butylbenzylmagnesium chloride + p-isopropylbenzaldehyde → dehydration → recrystallization |
| D | (p-t-butylphenyl)–CH=CH–(5,5,8,8-tetramethyl-5,6,7,8-tetrahydronaphth-2-yl) H | Liquid | — | 99.2% | p-t-Butylbenzylmagnesium chloride + 5,6,7,8-tetrahydro-5,5,8,8-tetramethyl-2-naphthaldehyde → recrystallization |

TABLE 3-continued

| Example | Structure of 1,2-diarylethylene | MP | BP | Purity by HPLC | Preparation |
|---|---|---|---|---|---|
| E | [t-Bu-C6H4-CH=CH-(1-naphthyl)] | 90-91° C. | — | 99.62% | p-t-Butylmagnesium chloride + 1-naphthaldehyde → dehydration → recrystallization |
| F | [t-Bu-C6H4-CH=CH-C6H4-iso-C8H17] (60% of m-, 40% of p-compound) | 82-86° | 217-225° C. 0.05 mbar | 98.97% | Isooctylbenzyllithium + p-t-butylbenzaldehyde → dehydration |
| G | [t-Bu-C6H4-CH=CH-C6H4-C16H33] (60% of m-, 40% of p-compound) | Liquid | 284-300° C. 0.07 mbar | 99.68% | n-i-hexadecylbenzyllithium + t-benzaldehyde → dehydration |
| H | [1-naphthyl-CH=CH-C6H4-C16H33] (60% of m-, 40% of p-compound) | Liquid | 242-266° C. 0.11 mbar | 98.69% | Hexadecylbenzyllithium + 1-naphthaldehyde → dehydration |
| I | [t-Bu-C6H4-CH=CH-C6H4-N(C2H5)2] | 125-126° C. | 175-187° C. 0.05 mbar | 99.18% | p-t-Butylmagnesium chloride + p-diethylaminobenzaldehyde → acetylation → thermolysis at 280-300° C. |
| J | [2-pyridyl-CH=CH-C6H4-C16H33] (60% of m-, 40% of p-compound) | Liquid | 285-305° C. 0.05 mbar | 73.62% | Hexadecylbenzyllithium + 2-pyridinaldehyde → acetylation → thermolyzation |
| K | [C6H5-CH=CH-C6H4-C16H33] (60% of m-, 40% of p-compound) | Liquid | 227-248° C. 0.05 mbar | 99.58% | n- + i-hexadecyltoluenelithium + benzaldehyde → acetylation → thermolysis |
| L | [C6H5-CH=CH-C6H4-C10H21] (60% of m-, 40% of p-compound) | Liquid | 218-222° C. 0.10 mbar | 98.19% | n- + i-Decyltoluenelithium + benzaldehyde → acetylation → thermolysis |
| M | [C6H5-CH=CH-C6H4-C14H29] (60% of m-, 40% of p-compound) | Liquid | 230-238° C. 0.2 mbar | 98.37% | n- + i-tetradecyltoluenelithium + o-methoxybenzaldehyde → acetylation → thermolysis |
| N | [(C2H5)2N-C6H4-CH=CH-C6H4-C14H29] (60% of m-, 40% of p-compound) | Liquid | 270-298° C. 0.45 mbar | 100% | n- + i-Tetradecyltoluenelithium + p-diethylaminobenzaldehyde → acetylation → thermolysis |

The solvents (benzene, cyclohexane, methylcyclohexane, octane, tetrahydrofuran, diethyl ether, dibutyl ether, diisopropyl ether, triethylamine) were freed from impurities by distillation with sufficient butyllithium and a small amount of styrene as indicator as to leave a permanent orange color.

Dimethyl ether, which boils at −25° C., was taken from a pressure flask, purified in a wash bottle charged with sec-butyllithium/methylcyclohexane solution and introduced into the reactor in gas form.

Nitrogen was washed with a mixture of white mineral oil, 1% by weight of styrene and 5% by weight of lithium butyl.

Lithium was used in the form of granules from Merck-Schuchardt from 1 to 5 mm in size.

Sodium was used in the form of an alloy with potassium in a molar ratio of 1:1.

The polymerization runs were carried out with commercial butadiene and styrene. Prior to use, the monomers were purified by distillation after addition of 0.5% by weight of triisobutylaluminum.

The functionalizing reagents used were 1,5-diazobicyclo[3.1.0]hexane from European Patent Application 87 103 893 hereinafter referred to as propylenediaziridine, and commercial ethylene oxide from a steel flask.

Analytical a) Characterization of catalysts according to the invention aa) Determination of the polymerization activity (PA)

PA is the level of polymerization-active lithium. 1 mol of difunctional catalyst thus corresponds to 2 mol of PA.

A calibrated 5 ml disposable polypropylene syringe (from Braun-Melsungen AG, West Germany) with a 15 cm long needle was used under inert conditions (the syringe is freed from contamination by repeated filling and emptying) to remove an amount of solution containing about 2–3 mmol of PA from the reactor or storage vessel and introduce the sample through a rubber septum into a 250 cm flask which is purged with pure nitrogen and in which 100 ml of toluene are being stirred with a magnetic stirrer. Contaminants in the toluene have previously been titrated away with the reaction solution to a pale yellow end point. The intensely colored solution is then titrated with 1N isopropanol in absolute toluene from a 5 cm$^3$ capacity calibrated injection syringe to a colorless end point. The total amount of PA in the reactor is then given by Σ reservoir+sample (cm$^3$)×cm$^3$ of 1N i-propanol=mmol of PA cm$^3$ of sample Determination of alkali content ab)

An amount of catalyst solution corresponding to approximately 1 mmol of PA is taken as described under aa) and introduced under nitrogen into a mixture of 10 cm$^3$ cyclohexane and 1 cm$^3$ or methanol. The colorless solution is then extracted with 20 cm$^3$ of distilled water. After the phases have separated, the clear aqueous extract is removed with an injection syringe and extracted twice more with 10 cm$^3$ of water each time. The combined extracts are then boiled in a conical flask until the organic solvents have been removed. After cooling, the residue is titrated with N/10 HCl and phenolphthalein until neutral. Σ reservoir+sample (cm$^3$)×cm$^3$ of N/10 HCl=mmol of alkali cm$^3$ of sample×10 ac) Determination of ether or tertiary amine in the catalyst 5 cm$^3$ of catalyst solution containing about 1–3 mmol of PA are titrated in a 25 cm$^3$ capacity distillation flask under nitrogen with ×cm$^3$ of a solution of 1N isopropanol in toluene until colorless. The entire solvent is then driven out into a receiver cooled with a methanol/carbon dioxide mixture, and the level of ether or amine in % by weight is determined in the distillate by gas chromatography. The gas chromatograph used, at 60° C., was a GC-3BT model from Shimadzu equipped with Carbowax 20M column.

The molar ratio of ether/polymerization activity (PA) is given by $$\frac{\% \text{ by weight of ether/tertiary amine} \times (5 + X) \text{ cm}^3}{\text{mmol of } PA \times 7.2} = \frac{\text{mmol of ether/tertiary amine}}{PA}$$

b) Characterization of polymers according to the invention ba) Determination of the molecular weight (MW) by GPC The determination was carried out on non-functionalized samples. The GPC instrument used was from Waters. The molecular weights were determined with reference to calibration curves by comparison with standardized, calibration polymers (cf. G. Glöckner, Polymercharakterisierung durch Flüssigkeitschromatographie, Verlag A. Hüthig, Heidelberg, 1982). The measurement was carried out in 0.25% strength solution in THF at 23° C. with a flow rate of 1.2 cm$^3$/min.

Block copolymer MWs were arrived at empirically by arithmetically averaging the calibration curves of the two homopolymers in accordance with the composition.

bb) Determination of the viscosity number

The viscosity number (VN) was determined at 25° C. in toluene (0.5 g of polymer in 100 cm$^3$ of toluene) in accordance with German Standard Specification DIN 51562.

bc) Determination of the nitrogen content

The total nitrogen content was determined by the Kjeldahl method.

bd) Determination of the mechanical properties

The mechanical data (tensile strength at 300% elongation, breaking strength and elongation at break) were determined on test specimens punched in accordance with German Standard Specification DIN 53455 out of 2 mm thick sheets or films molded between Teflon disks at 170°–180° C. at 60 bar (sheets) or 150° C. at 10 bar (film).

be) Crosslinking with diisocyanate 5 g of the polymer were dissolved in 25 cm$^3$ of dry cyclohexane, and to the solution was added 0.33 mmol of a solution of toluylene diisocyanate (TDI) in cyclohexane. After mixing the mixture was cast onto siliconized paper and dried at room temperature.

bf) Degradation of butadiene/styrene block copolymers and determination of the molecular weight of the polystyrene blocks The method of oxidative degradation of the polybutadiene moiety with peroxide/osmium tetroxide is described in detail by P. Kubin-Eschger, Angew. Makromol. Chem. 26 (1972), 207, so that no details need be given here.

bg) Determination of the OH number

To determine the OH number, the reprecipitated polybutadiene oils were initially stirred in the melt at 140° C. under a pressure of 0.4 mbar until all the volatiles had been removed and gas evolution had ceased. About 2 g of the oil were dissolved under ultrapure nitrogen in highly purified cyclohexane in a 250 cm³ flask, and the solution was mixed with 50 cm³ of THF. 0.5 cm³ of 1,1-diphenylethylene as indicator was added, and the solution was titrated with a 0.1N solution of n-butyllithium in cyclohexane until the appearance of a pale orange color. The titration was carried out through a rubber septum with a calibrated syringe. A blank value determined in the same way was subtracted from the consumption figure found.

The method had beforehand been checked for suitability by ¹H-NMR spectroscopy.

In the ¹H-NMR spectra of the OH-terminated polybutadienes the methylene protons of the —$CH_2$—OH group appear as a distinctly separate absorption at 3.6 ppm. From the intensity ratio of these resonances compared with the absorptions of the polybutadiene main chain it is possible to calculate the level of OH groups, expressed as the OH number. The details of the method can be found for example in Spektroskopische Methoden in der organischen Chemie by Manfred Hesse, Herbert Meier, Bernd Zeck, Georg Thieme Verlag, Stuttgart—New York, 3rd edition 1987. cf. also for example Pol. J. 17, No. 8, 977-980 (Short Comm.).

EXAMPLES 14–29

Examples 14–29 deal with the preparation of catalysts according to the invention. The reactor used is a 500 cm³ four-necked flask equipped with a magnetic stirrer (without Teflon sheathing), a thermometer and a rubber septum sealed port and which can be flushed with pure nitrogen. The reactor sits in a coolable water bath.

The reactor is charged either with highly purified ether or tertiary amine in an amount corresponding to the molar ratio indicated in Table 4, with or without methylcyclohexane or other inert hydrocarbons and about 2.0 g of commercial lithium granules. 50 mmol of the substituted 1,2-diarylethylene are added. The reaction starts at 25° C., either immediately or within 15 minutes, depending on the purity of the starting materials, with discoloration of the contents and an exothermic response. The reactor is cooled with water in such a way that 25° C. is not exceeded. The reaction has ended when the internal temperature and the bath temperature are back in agreement, in general after from 30 minutes to one hour. The solution is analyzed for PA and Li. In the runs identified in Table 4 by a), a portion of catalyst solution containing 50 mmol of PA (about 50 mm³) was transferred to a 250 mm³ distillation flask supporting an insulated column 20 mm in diameter and 30 cm in length packed with Sulzer metal packing. The reflux condenser is cooled with brine at −20° C. The distillation apparatus has beforehand been cleaned by boiling out with a lithium butyl solution. After addition of 100 mm³ of methylcyclohexane, the ether or THF was distilled out of the catalyst solution under a gradually reducing pressure at a reflux ratio of about 1:10 in such a way that the temperature at the base of the column does not exceed 20°-25° C. The distillation is continued until the temperatures at the top of the column and at the base of the column are identical.

Table 4 indicates the level of polymerization activity (PA) and of lithium in % of theory (degree of conversion), color and consistency of the catalysts and further relevant data.

TABLE 4

| Example No. | SDAE[1] (No. of Table 1) | Polar solvent (PS) Name | Molar ratio PS/SDAE | Apolar solvent | Degree of conversion in % of theory PA | Li content | Catalyst solution Concentration Mol of PA/L | Color | Consistency |
|---|---|---|---|---|---|---|---|---|---|
| 14 | A | THF | 20 | — | 98.4 | — | 0.62 | " | Solution |
| 14A[3] | A | THF | 1 | Methylcyclohexane | 95 | 95 | 0.34 | " | Thick suspension |
| 15 | A | DMEA[4] | 9 | Benzene | 100 | 99 | 2.28 | " | Thick suspension |
| 16 | B | THF | 10 | Methylcyclohexane | 95 | 98 | 0.52 | " | Solution |
| 16[3] | B | THF | 1.54 | Methylcyclohexane | 100 | 93 | 0.25 | " | Suspension |
| 17 | B | THF | 3 | Methylcyclohexane | 85 | 92 | 0.87 | " | Suspension |
| 18 | C | THF | 10 | Methylcyclohexane | 94 | 92 | 0.43 | " | Solution |
| 18a[3] | C | THF | 1.5 | Methylcyclohexane | 96 | — | 0.3 | " | Suspension |
| 19 | D | THF | 10 | Methylcyclohexane | 96 | 96 | 0.47 | " | Solution |
| 19a[3] | D | THF | 1.27 | Methylcyclohexane | 100 | 100 | 0.4 | " | Suspension |
| 20 | E | THF | 6 | — | 97.5 | 100 | 2.0 | Bluish black | Solution |
| 21 | E | THF | 3 | Methylcyclohexane | 80 | — | 1.5 | Bluish black | Suspension |
| 22 | I | THF | 6 | — | 106 | 100 | 2.2 | Brownish black | Solution |
| 22a[3] | I | THF | 1.5 | Methylcyclohexane | 100.75 | 97.5 | 2.2 | Brownish black | Suspension |
| 23 | G | DEE[5] | 2 | Methylcyclohexane | 100.5 | 97 | 2.5 | Brownish black | Solution |
| 23a | G | DEE[5] | 0 | Methylcyclohexane | 106 | 99.8 | 1.2 | Brownish black | Solution |
| 24 | F | THF | 2 | Methylcyclohexane | 99 | 101 | 2.36 | Brownish black | Solution |
| 25 | J | DEE[5] | 6 | Methylcyclohexane | 99.2 | 92 | 1.0 | Blackish brown | Solution |
| 26 | K | DEE[5] | 4 | Methylcyclohexane | 104.4 | 100.1 | 1.2 | Blackish brown | Solution |
| 26a[3] | K | DEE[5] | 0.09 | Methylcyclohexane | 100 | 100 | 0.4 | Blackish brown | Solution |
| 27 | M | DEE[5] | 4 | Methylcyclohexane | 99.6 | 99 | 1.2 | Blackish brown | Solution |

TABLE 4-continued

| Example No. | SDAE[1] (No. of Table 1) | Polar solvent (PS) Name | Molar ratio PS/SDAE | Apolar solvent | Degree of conversion in % of theory PA | Li content | Catalyst solution Concentration Mol of PA/L | Color | Consistency |
|---|---|---|---|---|---|---|---|---|---|
| 27a[3] | M | DEE[5] | 0.03 | Methylcyclohexane | 104.4 | 99 | 0.8 | Blackish brown | Solution |
| 28 | N | DEE[5] | 4 | Methylcyclohexane | 101.6 | 97 | 1.1 | Blackish brown | Solution |
| 28a[3] | N | DEE[5] | 0.17 | Methylcyclohexane | 100 | 101.5 | 0.45 | Blackish brown | Solution |
| 29 | L | DEE[5] | 4 | Methylcyclohexane | 101 | 99 | 1.2 | Blackish brown | Solution |
| 29a[3] | L | DEE[5] | 0.0 | Methylcyclohexane | 100 | 99 | 0.8 | Blackish brown | Solution |

[1]SDAE = substituted diarylethylene
[2]Theory = 2 mol per mol of SDAE
[3]PS distilled off under reduced pressure
[4]Dimethylethylamine
[5]Diethyl ether

EXAMPLE 30

Preparation of a disodium catalyst

The procedure of Example 29 is followed, except that dimerization is effected with 13 g of a liquid alloy containing sodium and potassium in a molar ratio of 1:1. The alkenylaromatic used was the diaryl-1,2-ethylene K from Table 3. The reaction is over after 30 minutes with complete conversion. The blackish brown solution contained 100 mmol of PA and 99 mmol of alkali, the concentration being 1.2 mol of PA/l.

EXAMPLE 31

Preparation of a low-ether catalyst with dimethyl ether (DME)

The reactor of Example 1 was charged with 14 cm³ of methylcyclohexane and 50 mmol of SDAE No. L of Table 3, and purified dimethyl ether gas was passed over the thoroughly mixed liquid. The reaction starts after 5 minutes with a rise in temperature of 21.5° to 23.5° and has gone to completion after one hour. Measurement shows a PA content of 98.4 mmol and a lithium content of 97.4 mmol.

The reactor contents are transferred by rinsing with 10 cm³ of methylcyclohexane into the distillation flask, and 40 cm³ of the flask contents are distilled off at an internal temperature of around 0° C. with stirring at an eventual pressure of 10 mmHg. After the pressure has been brought back to atmospheric, the solution is diluted with 40 cm³ of methylcyclohexane and transferred with rinsing into a stock reservoir vessel under pure nitrogen, and the contents are made up to 150 cm³. Concentration: 0.65 mol of PA/l. Polymerization experiments

EXAMPLES 32–44

The polymerization work was carried out in a reactor comprising a 10-l glass flask equipped with a heating-/cooling jacket, a stirrer, a brine reflux condenser operated with brine at −30° C., a calibrated dropping funnel likewise equipped with a brine reflux condenser, a rubber septum sealed port and pure nitrogen flushing means. The nitrogen is freed from traces of moisture and oxygen by washing with white mineral oil containing 2% by weight of lithium butyl.

The reactor is initially boiled out with a solution of lithium butyl in cyclohexane containing little styrene. The orange color which indicates the activity of the solution must be present right to the end. The solution is drawn off, and the reactor is charged with 3 l of cyclohexane purified beforehand by passage through a molecular sieve column. The impurities still present are titrated away at 40° C. with a catalyst solution according to the invention through the rubber septum using a calibrated syringe until a slight orange shade persists.

In the Examples, 3-block copolymers S-B-S composed of 50 or 27% by weight of styrene and 50 or 73% by weight of butadiene were prepared in a target molecular weight of 20,000 or 60,000. To this end, the reactor, after the impurities had been titrated away, was charged at the start temperatures indicated in Table 5 with about 50 cm³ of butadiene and the requisite amount of the particular catalysts (27 or 9 mmol of PA), and after the polymerization had started the remaining butadiene (in total 215 cm³ = 134.5 g or 300 cm³ = 187.5 g) was added at about 70° C. Afterwards the contents were maintained at 60° C. for one hour, a sample was removed, 148 cm³ = 134.5 g or 89 cm³ = 81 g of styrene were added, and polymerization was completed at from 50° to 60° C.

After 60 minutes the contents were cooled down to 40° C., a further sample was taken, and the orange polymerization solution was titrated with 1N isopropanol solution in cyclohexane using a calibrated syringe to a colorless end point in order to determine the catalyst reactivity still present at the end of the polymerization. The discontinued solution was then precipitated by pouring into 5 l of ethanol containing 0.5% by weight of di-t-butyl-p-cresol. After repeated kneading out with alcohol, the polymers were dried at 60° C. overnight in a vacuum drying cabinet.

Tables 5 and 6 below show the analytical data and the mechanical properties.

TABLE 5

Polymerization of 3-block styrene-butadiene-styrene copolymers: analytical data

| Catalyst of | Polar solvent (PS) (S: cyclohexane) Molar | Concentration | Start temperature | PA in % of | VN |

TABLE 5-continued

Polymerization of 3-block styrene-butadiene-styrene copolymers: analytical data

| Example No. | Example No. | Name | ratio PS:PA | in S mmol/l | of polymerization | starting PA[2] | of end product |
|---|---|---|---|---|---|---|---|
| 32 | 1 | THF | 20 | 172 | 20° | — | 33.4 |
| 33 | 3a | THF | 1.54 | 15.3 | 65° | — | 96.6 |
| 34 | 5a | THF | 1.5 | 8.3 | 65° | — | 95.7 |
| 35 | 9 | THF | 6 | 28 | 40° | 97 | 93.4 |
| 36 | 9a | THF | 1.5 | 6.7 | 40° | 95 | 107.5 |
| 37 | 10 | DEE | 2 | 9.5 | 40° | 97 | 96.7 |
| 38 | 10a | DEE | 0 | 0.0 | 75° | 96 | 123.1 |
| 39 | 11 | THF | 2 | 9.4 | 40° | 97 | 98.8 |
| 40 | 13 | DEE | 4 | 17.6 | 65° | 87.5 | 110.0 |
| 41 | 13a | DEE | 0.09 | 0.41 | 74° | 90 | 130.5 |
| 42 | 14a | DEE | 0.02 | 0.1 | 75.5° | 97 | 135.4 |
| 43 | 15 | DEE | 4 | 17.6 | 74.5° | 97 | 134.4 |
| 44 | 15a | DEE | 0.17 | 0.8 | 75 | 97.5 | 136.8 |

| | | | | GPC MWs × $10^{-3}$ | | | | | |
|---|---|---|---|---|---|---|---|---|---|
| | | | | | OsO$_4$ degradation of polystyrene | | | | |
| Example No. | PB block | | End Product | | Level wt. % | | MW × $10^{-3}$ from VN | | Remarks |
| | calc. | found[2] | calc. | found[2] | calc. | found | calc.[3] | found | |
| 32 | 10 | 14 | 20 | 22 | 50 | 53.1 | 5.5 | 8.5 | Product tough + elastic |
| 33 | 45 | 65 | 60 | 80 | 27 | 26.2 | 9 | 11.5 | Product tough + elastic |
| 34 | 45 | 55 | 60 | 80 | 27 | 28.8 | 12 | 13 | Product tough + elastic |
| 35 | 45 | 67 | 60 | 90 | 27 | 26.1 | 12.2 | 11 | Product tough + elastic |
| 36 | 45 | 70 | 60 | 95 | 27 | 26.9 | 12.8 | 11 | Product tough + elastic |
| 37 | 45 | 76 | 60 | 100 | 27 | 26.0 | 13.5 | 13 | Product tough + elastic |
| 38 | 45 | 70 | 60 | 95 | 27 | 24.8 | 12.8 | 12 | Product tough + elastic |
| 39 | 45 | 70 | 60 | 95 | 27 | 26.0 | 12.8 | 12 | Product tough + elastic |
| 40 | 45 | 80 | 60 | 110 | 27 | 25.9 | 14.9 | 12 | Product tough + elastic |
| 41 | 45 | 80 | 60 | 100 | 27 | 27.2 | 13.5 | 17 | Product tough + elastic |
| 42 | 45 | 88 | 60 | 120 | 27 | 26.5 | 16.2 | 17 | Product tough + elastic |
| 43 | 45 | 82 | 60 | 110 | 27 | 28 | 14.9 | 14 | Product tough + elastic |
| 44 | 45 | 90 | 60 | 120 | 27 | 25.4 | 16.2 | 17 | Product tough + elastic |

[1]Determined after polymerization by back titration with isopropanol - see text.
[2]Calculated from the ratio of initiator to monomer fopr Mw/Mn = 1
[3]The MW of the polystyrene blocks was calculated for the GPC MWs of the end products of polymerization on the assumption that both chain ends are polystyrene blocks.
THF = Tetrahydrofuran
DE = Diethyl ether

TABLE 6

Mechanical properties and configuration

| No. | Tensile strength at 300% elongation N/mm$^2$ | Breaking strength N/mm$^2$ | Elongation at break (%) | Butadiene configuration FTIR[2] | | |
|---|---|---|---|---|---|---|
| | | | | % 1,4-trans | % 1,2- | % 1,4-cis |
| 38 | 2.28 | 11.2 | 1660 | 58.2 | 10 | 31.8 |
| 40 | 2.42 | 12.4 | 1340 | 32.5 | 46 | 21.5 |
| 41 | 2.25 | 11.6 | 1352 | 59 | 11 | 30 |
| Comparison[1] | 1.95 | 9.62 | 577 | 57.4 | 12.2 | 30.4 |

[1]The SBS 3-block copolymer of 27% by weight of styrene, 73% by weight of butadiene and MW 68,000 was prepared with lithium butyl by successive polymerization of styrene-butadiene-styrene in cyclohexane at 70° C. in a conventional manner.
[2]FTIR = Fourier transform infrared spectroscopy The data reveal that the polymers prepared with catalysts according to the invention are superior to the comparison in mechanical properties.

EXAMPLE 45

A 500 cm$^3$ flask equipped with a magnetic stirrer, a water bath, a thermometer and nitrogen flushing means was charged with 100 cm$^3$ of purified toluene, titrated with the catalyst solution of Example 30 (disodium catalyst) to a slight orange shade using a calibrated syringe inserted through a rubber septum and immediately admixed with 0.77 cm$^3$ (0.5 mmol of PA) of catalyst solution. Polymerization was effected at 50° C., the polystyrene was precipitated by pouring with thorough stirring into ethanol, washed on the suction filter with alcohol and dried. GPC indicated an MW of 63,000 (calculated at 40,000).

EXAMPLE 46

Preparation of a terminally amino-functionalized polybutadiene oil

The apparatus of Example 32, except that it had been equipped with a crossbar metal stirrer for particularly thorough mixing and application of a high torque, was charged with 3000 cm$^3$ of cyclohexane and 50 cm$^3$ of butadiene at 65° C., and 16.5 mmol of the catalyst (33 mmol of PA) of Example 26 were added, followed at that temperature by a further 83 cm$^3$ (together 83 g) of butadiene in such a way that reflux was just avoided. After the addition was complete, the contents were held at 60° C. for 30 minutes to complete the polymerization then cooled to 40° C. and functionalized with 40 mmol of propylenediaziridine, and the solution became a viscose gel. After 30 minutes of stirring, the reactor contents were precipitated with 2 l of ethanol. The polybutadiene oil which settles out is stirred 3 times with methanol, mixed with 0.2 g of di-t-butyl-p-cresol and dried at 60° C. under reduced pressure. The result is a pourable polybutadiene oil of MW 6000 (GPC) and a narrow MW distribution. The Kjeldahl nitrogen content is 0.85% (theory: 0.93%). FTIR analysis indicates a configuration of 41.4% of 1,2-cis, 23.4% of 1,4-cis and 35.5% of 1,4-trans for the incorporated polybutadiene.

4 mmol of hexamethylene diisocyanate (0.6 g) were rapidly stirred into 5 g of the oil in a penicillin glass at room temperature with a glass rod, and the mixture was poured onto silicone paper. The mixture became solid within minutes to form a colorless, elastic rubber.

EXAMPLE 47

Preparation of an OH-functionalized polybutadiene oil

The procedure of Example 46 was followed, except that the functionalizing propyleneaziridine was replaced by 400 mmol of ethylene oxide. In this case, there was an even higher increase in the viscosity than in Example 46 with the material becoming aspic-like. After stirring for 1 hour to ensure complete mixing and reaction, the polymerization is discontinued by addition of a few cm$^3$ of methanol, and a mobile solution forms. The incorporated polybutadiene is 39% 1,2-cis, 24% 1,4-cis and 37% 1,4-trans. The polybutadiene oil has an MW (GPC) of 6200 and an OH number of 16.

We claim:

1. A stilbene compound of the formula Ia $$R^1R^2R^3Ar^1\text{---}CH\text{=}CH\text{---}Ar^2R^4R^5R^6 \quad (Ia)$$

wherein $Ar^1$ and $Ar^2$ are identical or different aromatic or quasi-aromatic radicals, $R^1$ to $R^6$ are each hydrogen or linear or branched alkyl, alkenyl, aralkyl or cycloalkyl radicals of from 1–25 carbon atoms, or these radicals also containing ether linkages or tertiary amino substituents, or these substituents forming ring linkages with the Ar radicals having 3 or more aliphatic carbon atoms, and where at least one of the radicals $R^1$ to $R^6$ is hydrocarbon-solubilizing alkyl, alkoxy or dialkylamino of 4 or more carbon atoms in the alkyl moiety.

2. The stilbene compound according to claim 1, of the formula

3. The stilbene compound according to claim 1, of the formula

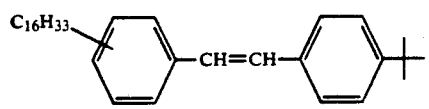

4. The stilbene compound according to claim 1, of the formula

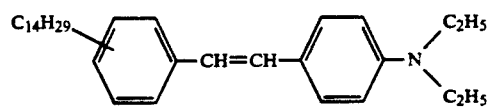

5. The stilbene compound according to claim 1, of the formula

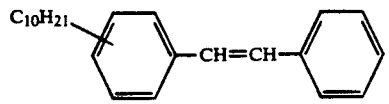

6. The stilbene compound according to claim 1, of the formula

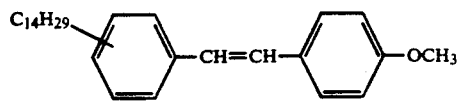

7. The stilbene compound according to claim 1, of the formula

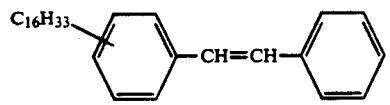

8. The stilbene compound according to claim 1, of the formula

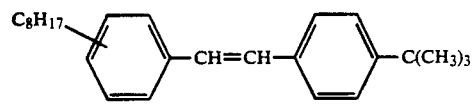

9. The stilbene compound according to claim 1, of the formula

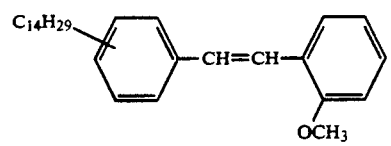

10. The stilbene compound according to claim 1, of the formula

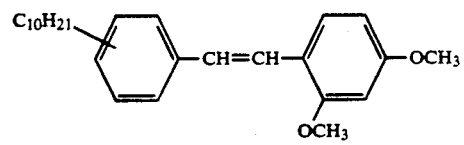

11. The stilbene compound according to claim 1, of the formula

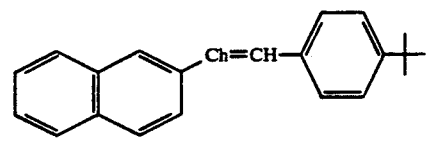

12. The stilbene compound according to claim 1, of the formula

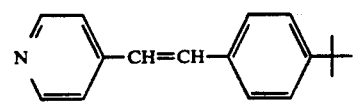

* * * * *

UNITED STATES PATENT AND TRADEMARK OFFICE
CERTIFICATE OF CORRECTION

PATENT NO. : 5,081,251
DATED : January 14, 1992
INVENTOR(S) : Dietmar Bender et al.

It is certified that error appears in the above-identified patent and that said Letters Patent is hereby corrected as shown below:

On the Title page, item [54] and col. 1
   The title is incorrect, should be, --STILBENE COMPOUNDS USEFUL IN ANIONIC POLYMERIZATION--.

Signed and Sealed this

Twenty-fifth Day of May, 1993

Attest:

MICHAEL K. KIRK

*Attesting Officer*       Acting Commissioner of Patents and Trademarks